United States Patent
Beacon et al.

[11] Patent Number: 5,935,086
[45] Date of Patent: Aug. 10, 1999

[54] ORTHOPAEDIC MEASUREMENT AND DISPLAY SYSTEM

[76] Inventors: Jonathan Paul Beacon, Sewell Manor, Sewell, Dunstable, Bedfordshire, United Kingdom; Jacques Phillipe Laboureau, 24 rue Fontaine Biffenois, F-21000 Dijon, France; Raymond Clarence Chance Wadey, 18 Greatwoods, Edington, Near Westbury Wiltshire, United Kingdom

[21] Appl. No.: 08/551,465

[22] Filed: Nov. 1, 1995

[30]    Foreign Application Priority Data

Nov. 1, 1994 [GB] United Kingdom .................... 9422007

[51] Int. Cl.⁶ ...................................................... A61B 5/00
[52] U.S. Cl. .......................................................... 600/595
[58] Field of Search .................................. 128/774, 779, 128/782; 600/587, 592, 595

[56]    References Cited

U.S. PATENT DOCUMENTS

| | | | |
|---|---|---|---|
| 4,583,554 | 4/1986 | Mehelnan et al. .................. | 128/774 |
| 4,583,555 | 4/1986 | Malcom et al. .................... | 128/782 |
| 4,799,497 | 1/1989 | Riley ............................... | 128/774 |
| 4,804,000 | 2/1989 | Lamb et al. ........................ | 128/774 |
| 4,823,807 | 4/1989 | Russell et al. ..................... | 128/773 |
| 4,969,471 | 11/1990 | Daniel et al. ..................... | 128/782 |
| 5,228,454 | 7/1993 | Siegler ............................ | 128/782 |
| 5,263,492 | 11/1993 | Voyce ............................. | 128/782 |

OTHER PUBLICATIONS

In Vivo Knee Stability: "A Quantitative Accessment Using An Instrumented Clinical Testing Apparatus", authored by Markolf et al and publised in *The Journal of Bone and Joint Surgery*, vol. 60 A, No. 5, 1978.

In Vivo Rotatory Knee Stability: "Ligamentous And Muscular Contributions" by Shoemaker et al, in *The Journal of Bone and Joint Surgery*, vol. 64A, No. 2, 1982.

*Primary Examiner*—Max Hindenburg
*Attorney, Agent, or Firm*—Weintraub & Brady

[57]    ABSTRACT

A knee joint laxity measuring and displaying apparatus includes a housing 1 and a strap holder 2 interfixed by rods 3 and connectible to the lower leg by straps 15 and 16. A clinometer 11 mounted in the housing 1 measures internal-external rotation of the tibia with reference to the vertical. Electrical circuitry including the clinometer 11 compares actual readings with a zero reading and displays the difference. In a more advanced form of the apparatus, flexion and/or glide and glide force are measured and displayed.

14 Claims, 8 Drawing Sheets

ORTHOPAEDIC MEASUREMENT AND DISPLAY SYSTEM

BACKGROUND OF THE INVENTION

1. Field of the Invention

This invention relates to an orthopaedic measuring and displaying system.

2. Description of the Prior Art

U.S. Pat. No. 4,583,555 discloses a tibia-referenced system for objectively testing the integrity of the anterior and posterior cruciate ligaments of the knee with passive glide (i.e. drawer), active glide, and end point tests. Two simplified forms of the system embody an elongated reference arm with a distal end pad that is fulcrumed against a distal region on the tibia and a proximal reference pad that rests on either the tibial tubercle or patellar bone structure, while a displacement indicator rod slidably mounted on the arm carries another proximal reference pad that rests on the other of these two bone structures adjacent the knee joint. In a third form of intermediate complexity, the second reference structure, instead of the indicator rod, is a second elongated reference arm distally pivotally connected to the other reference arm, each of the two arms carrying a reference pad that rests on a respective one of the tibial tubercle and patellar bone structures; and in this form the relative angular pivotal positions of the arms is translated to a displacement indicator dial that provides a direct readout of anterior or posterior glide. The fourth and most complex form of the system has the distally pivoted reference arms and direct readout displacement indicator dial of the third form, and further includes a case in which the arms are pivoted that is strapped against the tibia, with a force-applying handle extending anteriorly of the case and force-indicating microswitches operatively arranged between the handle and the case to audibly indicate predetermined applied force levels.

The article "In Vivo Knee Stability" by Messrs. Markolf, Graff-Radford and Amstutz in the Journal of Bone and Joint Surgery, Vol. 60A (1978.07) No. 5, pages 664–674, discloses the use of a clinical testing apparatus to record anterior-posterior tibial force versus glide and varus-valgus moment versus angulation during manual manipulation of the knee. A modified dental chair served as the base for the apparatus. When the apparatus was positioned for glide testing, the knee was in 90° of flexion and the subject was seated erect with the thigh secured in an adjustable metal shell clamped to the chair and containing an inflatable pad, with the pelvis slid posteriorly against the seat back, a contoured metal patellar block covered with stiff padding was pressed against the patella and locked in position. The ankle was strapped securely to an adjustable foot rest. The examiner then applied glide force manually. When the glide test was performed with a 20° flexion angle, the foot rest again held the ankle rigidly. A heavy canvas strap behind the knee was used to hold the patella firmly against the pad. To apply glide force, a small, V-shaped, padded, aluminium plate was pressed against the anterior margin of the tibia just below the tibial tubercle and secured by a "VELCRO" strap around the calf. An instrumented force handle was connected to the plate and the glide force was recorded on the y-axis of the recorder. A spring-loaded plunger was positioned on the tibial tubercle and its shaft was connected to a card which passed over a pulley mounted on the shaft of a rotary potentiometer. The output of this potentiometer, which was calibrated to measure glide, was recorded on the x-axis of the recorder. Medial/lateral fixation of the femur was accomplished by medial and lateral femoral condylar clamps with pressure pads. Varus-valgus angulation of the tibia was recorded by a rotary potentiometer mounted on an aluminium frame and strapped to the tibia. The shaft of this potentiometer was connected to a four-bar linkage mounted on a rigid cross-bar fixed to the chair. For the application of medial-lateral force, the subject's shoe was clamped onto an adjustable holding plate. Medial and lateral force handles, screwed into vertical bars perpendicular to the plate, were located at approximately the level of the ankle. The force output was recorded on the y-axis of the recorder. The distance from the line of the applied force to the knee joint line was measured so that the varus-valgus bending moment at the knee could be calculated.

U.S. Pat. No. 4,306,571 discloses a three-plane goniometer including three small rotary potentiometers which are closely spaced together in a unit to measure rotation of the knee about three different axes, namely internal-external rotation angles, flexion-extension angles, and varus-valgus angles. The unit is primarily mounted on a cuff on the outside of the thigh. The mounting assembly for the three-plane goniometer includes a curved yoke where the ends of the yoke curve from the front to the rear, with the goniometer unit being held between the ends of the rearwardly extending arms of the yoke. Extending downwardly from the goniometer is a square rod which slidably engages a square hole in a nylon ball mounted in a two-axis gimbal, which is secured to a cuff strapped to the calf of the leg. Injuries may be diagnosed by comparing the pattern for one leg before injury with the pattern for that leg after injury or by comparing the pattern for one (healthy) leg with that for the other (injured) leg. The goniometer is mounted so that it may be readily reversed and used for both the right and left legs. Associated processing circuitry includes corresponding reversing circuits for conforming the plots for the right and left leg, and also includes special face marking circuitry. Comparative tests may be made for different types of footwear and athletic playing surfaces, and the torque which is produced may be compared to determine the preferred footwear or playing surface.

The article "In Vivo Rotatory Knee Stability" by Messrs. Shoemaker and Markolf in The Journal of Bone and Joint Surgery, Volume 64A, (1982.02), No.2, pages 208 to 216 discloses the use of a clinical testing apparatus to measure active and passive components of torsional stability of the knee, test curves being produced for torque versus internal-external rotation. The apparatus included a dental chair modified with a rigid cross bar, a thick, stationary, horizontal centre-pole and an adjustable vertical centre post. For a torsion test at 90° flexion, the subject's foot was secured to the chair foot-plate with "VELCRO" straps and raised metal shoe-stops clamped tightly against the foot. The knee was strapped firmly against a patellar pad held to the cross-bar with a dual-locking clamp. Tibial rotation was measured by a rotary potentiometer mounted in a housing contoured to fit against the tibial crest and strapped to the leg above the ankle. An additional potentiometer mounted to the heel of the foot-plate measured rotation of the foot. The potentiometer shafts were connected alternately to a four-bar linkage that was free to swing in the anterior-posterior plane through low-friction linear races mounted to the base of the foot-plate. Tibial torque was measured by an electrical torque-cell built into the middle of the shaft of the foot-plate. The distal end of the shaft allowed the foot-plate to be rotated manually with a handle or locked into place with a frictional split-clamp brake. To study 20° of flexion, the foot-plate was mounted to the adjustable vertical post. A contoured wooden block shaped and padded to contact the patella was clamped to the cross-bar, and a "VELCRO" strap held the knee firmly against the block. Medial and lateral femoral condylar clamps co-operated with the patellar block and strap to minimise the rotation of the femur in response to torque applied at the foot. Continuous measurements of applied torque versus induced rotation for movement of the tibia and the foot were plotted on an x-y recorder during cyclic loading by the examiner.

U.S. Pat. No. 4,583,554 discloses a knee ligament testing device for use in testing the anterior cruciate ligament of the knee. The device includes a force application arm and a reference arm which are hinged at a pivot joint. A predetermined maximum force can be applied to the force application arm by exerting force on a torque limiter inserted in an aperture in the force application arm. The torque limiter ensures that the identical force will be applied on a leg for every test to ensure reproducibility and prevents the application of excessive force to the leg. Displacement of the tibia relative to the femur is sensed by movement of an inner tube relative to an outer tube which is translated into rotational movement of an input shaft of an electrically linear, rotary potentiometer. The change in resistance in the potentiometer is analyzed and converted to a linear measurement which is displayed on a display.

U.S. Pat. No. 4,804,000 discloses an apparatus for electronically measuring ligamentous insufficiencies in the knee, the apparatus including an exoskeletal articulating framework that is secured above the knee to the patient's femur and below the knee to the tibia and has substantially skeletal conforming articulating joint members with measuring means for determining the relative motions of tibia to femur. The measuring means measure, in addition to anterior-posterior glide, varus-valgus laxity and internal-external rotation of the tibia while recording the flexion angle. They include a first radial transducer positioned at the axis of overall knee flexion to measure the flexion angle and alternate second and third radial transducers to selectively measure internal-external rotation or varus-valgus motion. The anterior-posterior glide is measured by a fourth transducer connected to a support linkage of a floating patellar pad positioned at the end of a tibial rod.

Although the apparatus of U.S. Pat. No. 4,306,571, U.S. Pat. No. 4,583,554 and U.S. Pat. No. 4,804,000 are much more portable and compact than the dental chair-based apparatus of the two journal articles, their measuring devices all require to be interposed between two driving elements themselves acting upon or acted upon by bones of the joint.

SUMMARY OF THE INVENTION

According to one aspect of the present invention, there is provided an apparatus for measuring an angle of turning of one bone of a joint about a substantially horizontal axis, comprising means for determining, said means for determining a first angular position of said one bone about said axis and determining a second angular position of said one bone about said axis, means for mounting, said means for mounting said means for determining upon said one bone, and means for automatic displaying, said means for automatic displaying the angle between said first and second angular positions, wherein said first and second angular positions are determined relative to the vertical.

According to another aspect of the present invention, there is provided a method of measuring an angle of turning of one bone of a joint about a substantially horizontal axis, the method comprising determining a first angular position of said one bone about said axis, turning said bone about said axis, determining a second angular position of said one bone about said axis, and automatically displaying the angle between the two positions, wherein the determining of the first and second angular positions is performed with reference to the vertical.

Owing to these two aspects of the invention, it is possible automatically to measure and display the angle of turning, to assist a user, particularly a surgeon, in reliably diagnosing whether and to what extent for example ligaments of the joint have been weakened or severed, without any need for complicated mechanical connections to provide driving forces for the determining means.

According to a third aspect of the present invention, there is provided an apparatus for applying and measuring glide force on a tibia of a knee joint, comprising means for applying force, means for mounting said means for applying force so that said means for applying force is movable relative thereto, and means for analog transducing, the means for analog transducing detecting linear load applied between said means for applying force and said means for mounting and emitting an electrical signal proportional to the load applied.

Owing to this aspect of the invention, it is possible automatically to measure and display the variation of the applied glide force in a continuous and simple manner.

BRIEF DESCRIPTION OF THE DRAWINGS

In order that the invention may be clearly understood and readily carried into effect, reference will now be made, by way of example, to the accompanying drawings, in which.

DESCRIPTION OF THE PREFERRED EMBODIMENTS

A basic form of the system to be described hereinafter serves automatically to measure and display the angle of rotation of the tibia about its own longitudinal axis relative to the femur for indication of weakened or severed cruciate ligaments. In an advanced form of the system, the angle of rotation of the tibia for a range of angles of flexion may be automatically measured and displayed and/or the maximum extent of glide of the tibia relative to the femur may be automatically measured and displayed.

Figure 1:
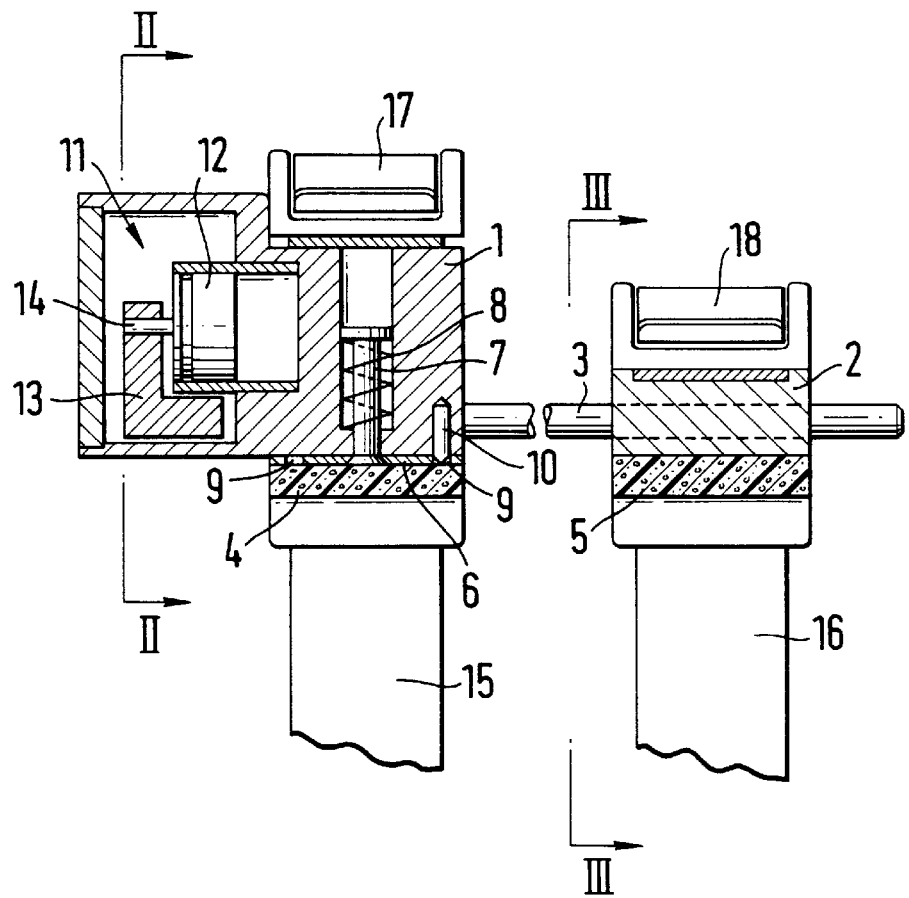
FIG. 1 shows a longitudinal diagrammatic section through a device for determining the angular position of rotation of a tibia near a knee joint, and forming part of a basic form of system for automatically measuring and displaying bone displaceability in a knee joint.
Figure 2:
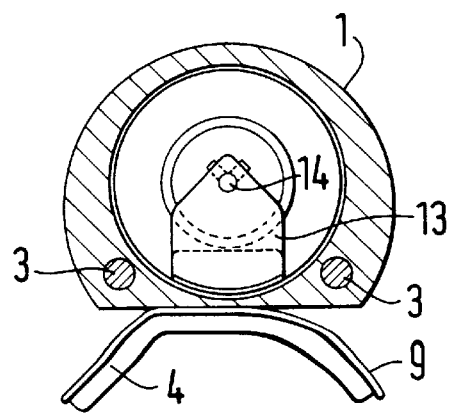
FIG. 2 shows a diagrammatic section taken on the line II—II of FIG. 1.
Figure 3:
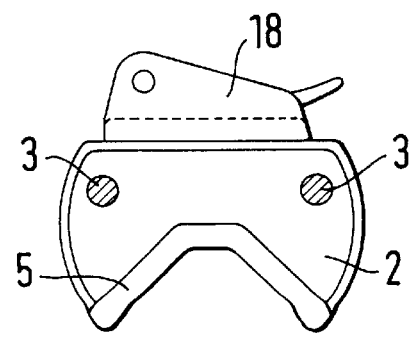
FIG. 3 shows a diagrammatic section taken on the line III—III of FIG. 1.

Referring to FIGS. 1 to 3, the device includes a proximal housing 1 and a distal holder 2 interconnected by a pair of parallel rods 3. The housing 1 and the holder 2 are each in the form of a yoke fitted with a foam-plastics pad 4, 5 to bear and locate against the shin. The pad 4 is mounted on a metal backing plate 6 which is resiliently carried on the housing by way of a central plunger 7 and a helical compression spring 8 and is formed with two detent holes 9 wherein a pin 10 fixed in the housing 1 can engage to locate the pad 4 and the plate 6 reversibly for application selectively to left and right legs. Mounted in the housing so as to have its axis of operation parallel to the rods 3 and thus to the tibia is a clinometer 11 comprising a rotary, electrically linear potentiometer 12 and a pendulum 13 fixed to a rotary input shaft 14 of the potentiometer 12. Each of the housing 1 and the holder 2 has a strap 15,16 anchored thereto and tightenable in a strap clip 17,18.

Figure 4:
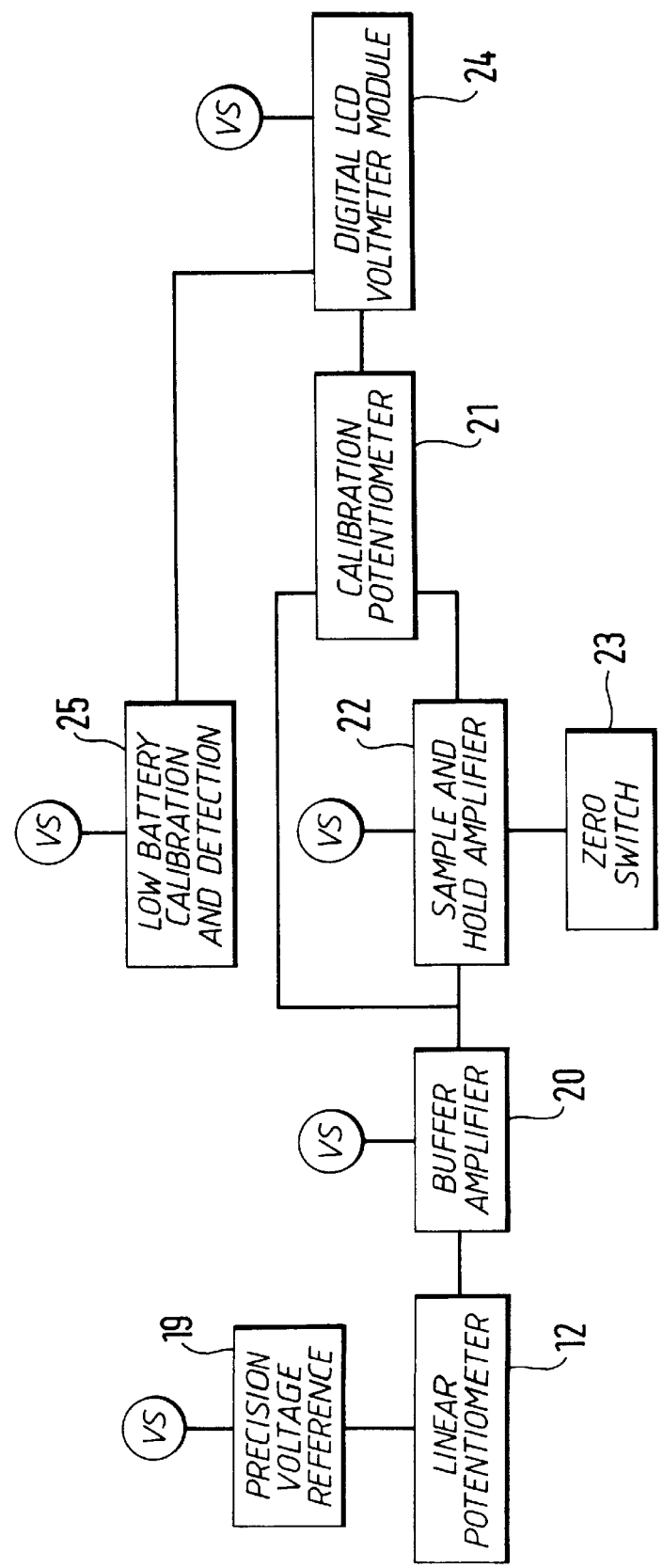
FIG. 4 shows an electrical circuit diagram of the basic form of system.

Referring to FIG. 4, in which "VS" refers to voltage supply, in this cane a battery, a precision voltage is supplied to the potentiometer 12 by a device 19. The output from the potentiometer 12, which is directly proportional to the tibial rotation angle, is fed to a buffer amplifier 20 which minimises the electrical load on the potentiometer 12. The output from the amplifier 20 is fed directly to a calibration potentiometer 21 as an actual reading output and to a sample and hold amplifier 22 which stores and outputs to the potentiometer 21 a zero (i.e. reference) angle set by the user's depressing a push-button zero switch 23. This calibration potentiometer 21 is adjusted by the manufacturer of the system to ensure that, when a particular angle is input into the potentiometer 12, a digital LCD (liquid crystal display) voltmeter module 24 displays exactly that angle. The potentiometer 21 acts as a comparator, its output fed to the module 24 being directly proportional to the actual positive or negative angle of rotation of the tibia from the zero, which is what the module 24 displays. A low battery calibration and detection device 25 connected to the module 24 is adjusted by the system manufacturer to set the minimum battery voltage acceptable and emits a warning when the battery voltage falls below that threshold.

Figure 5:
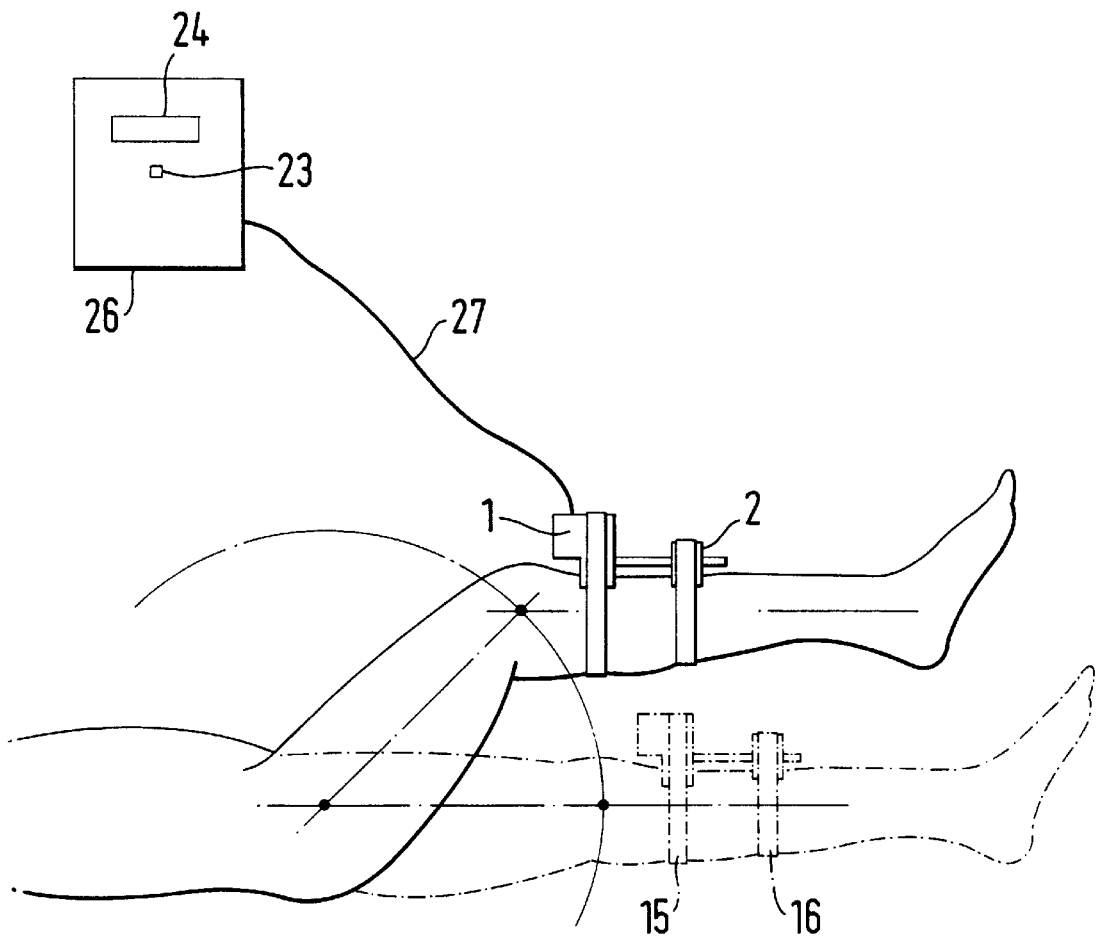
FIG. 5 is a side view of the basic form of system in use on a subject.
Figure 6:
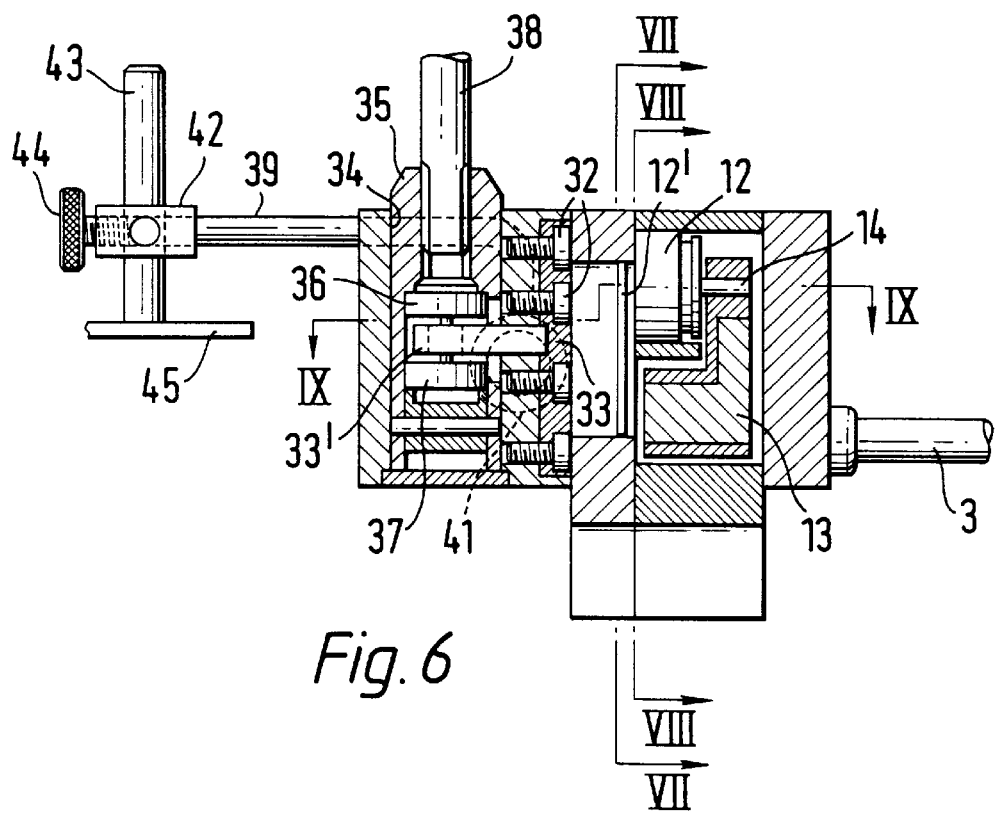
FIG. 6 is a view similar to FIG. 1, but of a device, in an advanced form of the system, for determining not only the angular position of rotation of the tibia but also glide displacement and glide force.
Figure 7:
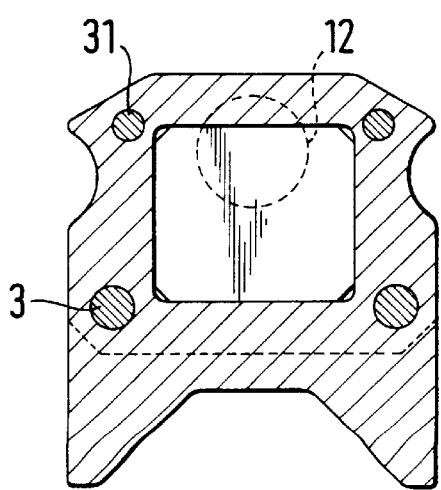
FIGS. 7 to 9 show diagrammatic sections taken on the lines VII—VII, VIII—VIII and IX—IX, respectively, of FIG. 6.
Figure 8:
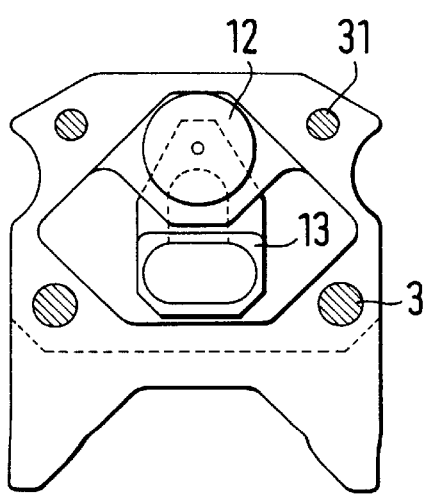
Figure 9:
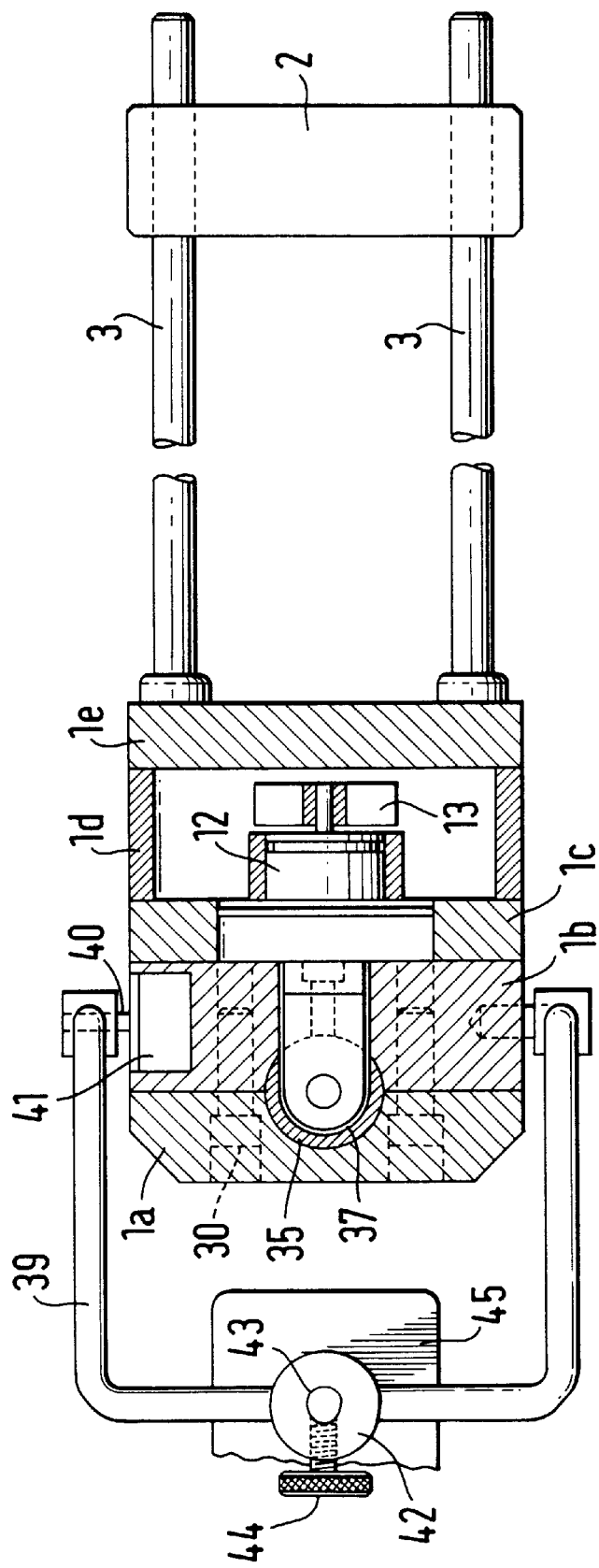

Referring to FIG. 5, the subject's leg is shown in two positions, one substantially horizontal and shown in chain lines and the other, shown in full lines, in flexion with the tibia horizontal. The device of FIGS. 1 to 3 is seen strapped to the lower leg adjacent the knee. A portable housing 26 containing the electrical circuitry of FIG. 4 (except for the potentiometer 12) is connected by an electrical cable 27 to the housing 1. The subject's leg is put into the horizontal position shown and the user employs his clinical judgment to set the tibia in the desired zero position of internal-external rotation and then operates the switch 23. The user can then rotate the tibia and the positive or negative angle of rotation automatically appears on the module 24. If the user wishes to ascertain variations of rotational laxity with angle of flexion, he keeps the tibia horizontal while raising and lowering the same to produce various angles of flexion.

The device of FIGS. 6 to 9 has all of the features 1 to 16 of FIGS. 1 to 3, except that some of them have been either omitted from the Figures or shown diagrammatically, for the sake of clarity. The housing 1 is assembled from a number of pieces 1a to 1e fastened together by screws 30 and 31. Mounted adjacent the potentiometer 12 is a printed circuit board (PCB) 12' for conditioning the output from the potentiometer 12. Fixed in the housing 1 by means of screws 32 is a beam 33 from which extends perpendicularly a reaction arm 33' fixed at one end to the beam. Slidably mounted in a bore 34 in the housing 1 is a sleeve 35 fixedly containing two pressure transducers 36 and 37, the transducer 36 serving for measuring posterior glide force exerted by the user upon a push-pull rod 38 fixed to the sleeve 35 and the transducer 37 serving for measuring anterior glide force exerted by the user upon the rod 38. The arrangement whereby the rod 38 carries two load cells 36 and 37 at opposite sides of the arm 33' is a simple way of providing for measurement of glide force in either sense. Instead of the load cells 36 and 37, one or two strain gauges carried by the arm 33' can be employed. A U-shaped yoke 39 of metal rod has outer end zones thereof extending perpendicularly to the general plane of the U and pivotally mounted on the housing 1 so as to be turnable about a medial-lateral axis. One of those ends is fixed to an input shaft 40 of a rotary potentiometer 41 serving to measure angular displacement of the yoke 39 and thereby measure glide. Fixed centrally of the base of the U is a bush 42 having its bore perpendicular to the general plane of the U and receiving a rod 43 adjustably fixed therein by means of a set screw 44 and carrying a patellar plate 45 for being pressed firmly against the patella by the user's hand. The single-bar link provided by the yoke 39 between the patellar element 45 and the rotary sensor 41 is a simple means of measuring glide under the force applied via the rod 38, since the maximum glide encountered is such that the angular motion of the plate 45 approximates to linear motion.

Figure 10:
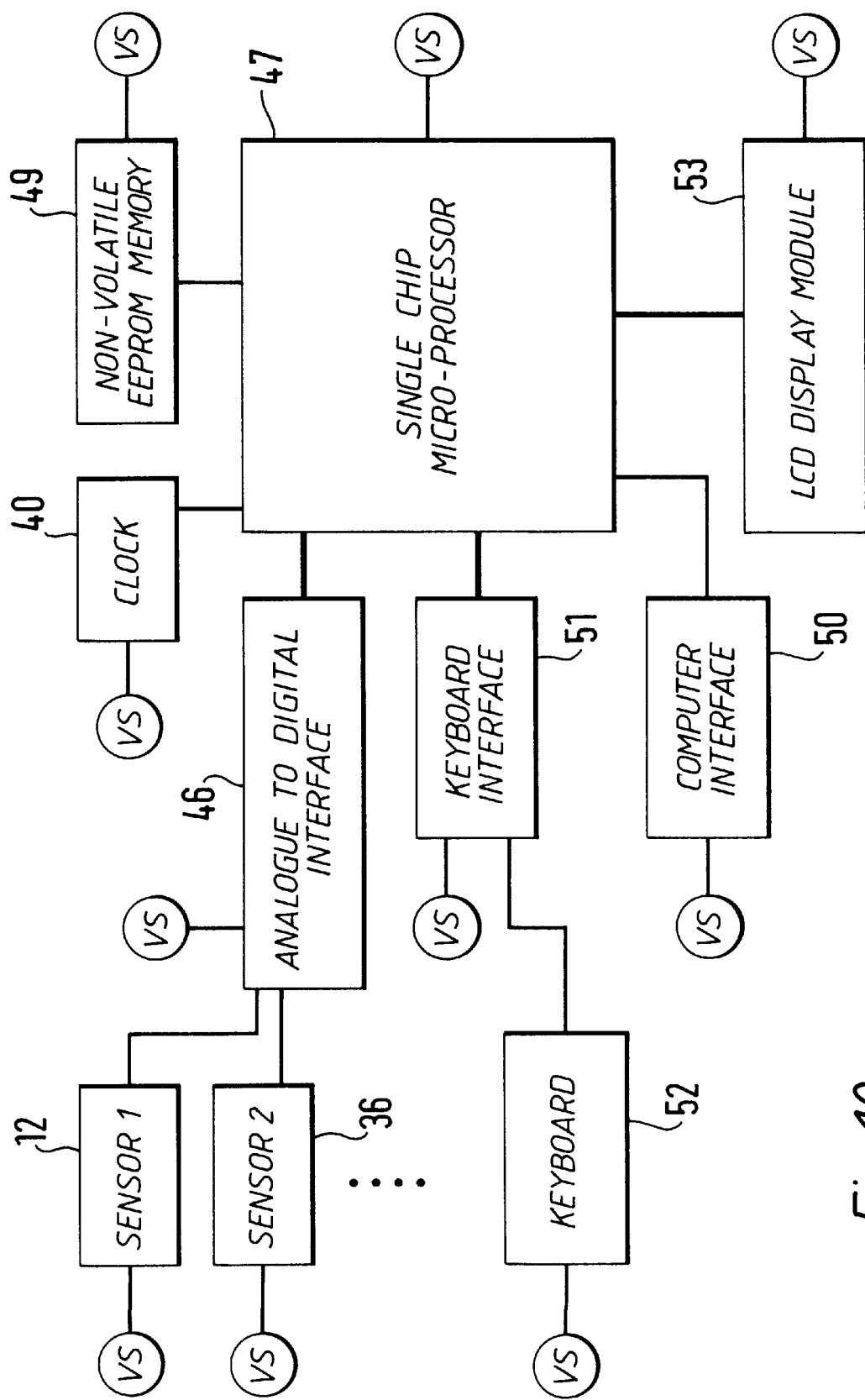
FIG. 10 shows an electrical circuit diagram of the advanced form of the system.

Referring to FIG. 10, there are shown a plurality of sensors which consist of the potentiometer 12, the transducers 36 and 37, the potentiometer 41 and one or two clinometers for measuring the flexion angle. The outputs therefrom are fed to an analogue-to-digital interface 46 and the digital signals fed to a single-chip microprocessor 47. Connected to the microprocessor 47 are a clock 48, an electrically erasable programmable read-only memory (EEPROM) 49, a computer interface 50, a keyboard interface 51 to a keyboard 52, and an LCD display module 53.

Figure 11:
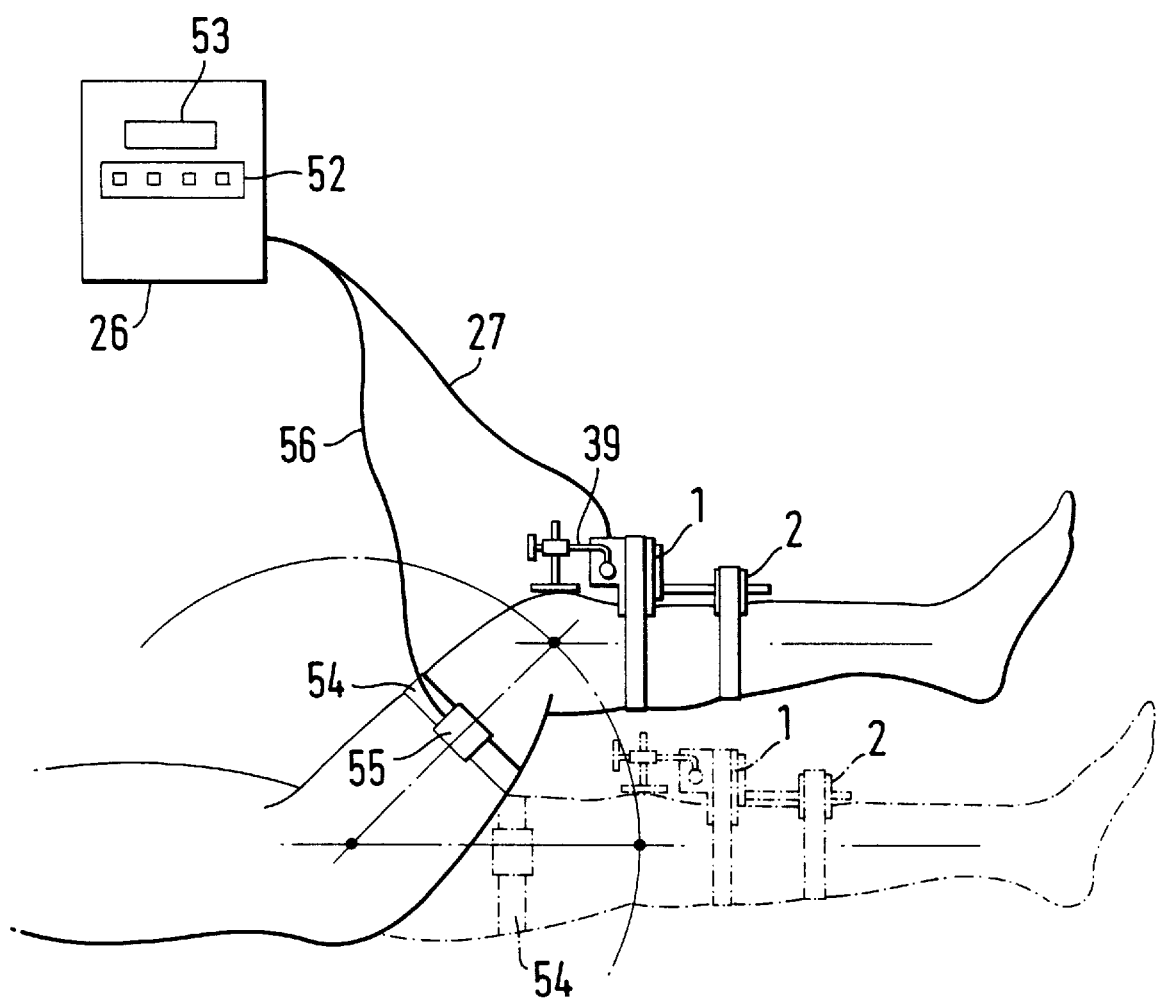
FIG. 11 is a side view of the advanced form of the system in use on a subject.

Referring to FIG. 11 for measuring the flexion angle, there is fastened to the subject's upper leg by means of a strap 54 a clinometer 55 also connected by an electrical cable 56 to the circuitry in the housing 26. In order to avoid the user's having to keep the tibia approximately horizontal during measurement at various flexion angles, another clinometer could be provided at the tibia to measure the angle of the tibia to the vertical, so that the difference between the outputs from the two flexion clinometers represents the flexion angle.

In the event that a glide test is not required, the yoke 39 can be swung out of the way.

The clinometers 11,55, etc. each continuously provide a vertical reference for rotation or flexion. Although each clinometer can take the form of a pendulum-cum-rotary potentiometer, it could take the form of an accelerometer chip, or be capacitive-based. Capacitive-based, liquid clinometers are sophisticated ways of measuring angles with respect to gravity. Advantages are that no mechanically moving apparatus within them is needed and they are small in size.

Figure 12:
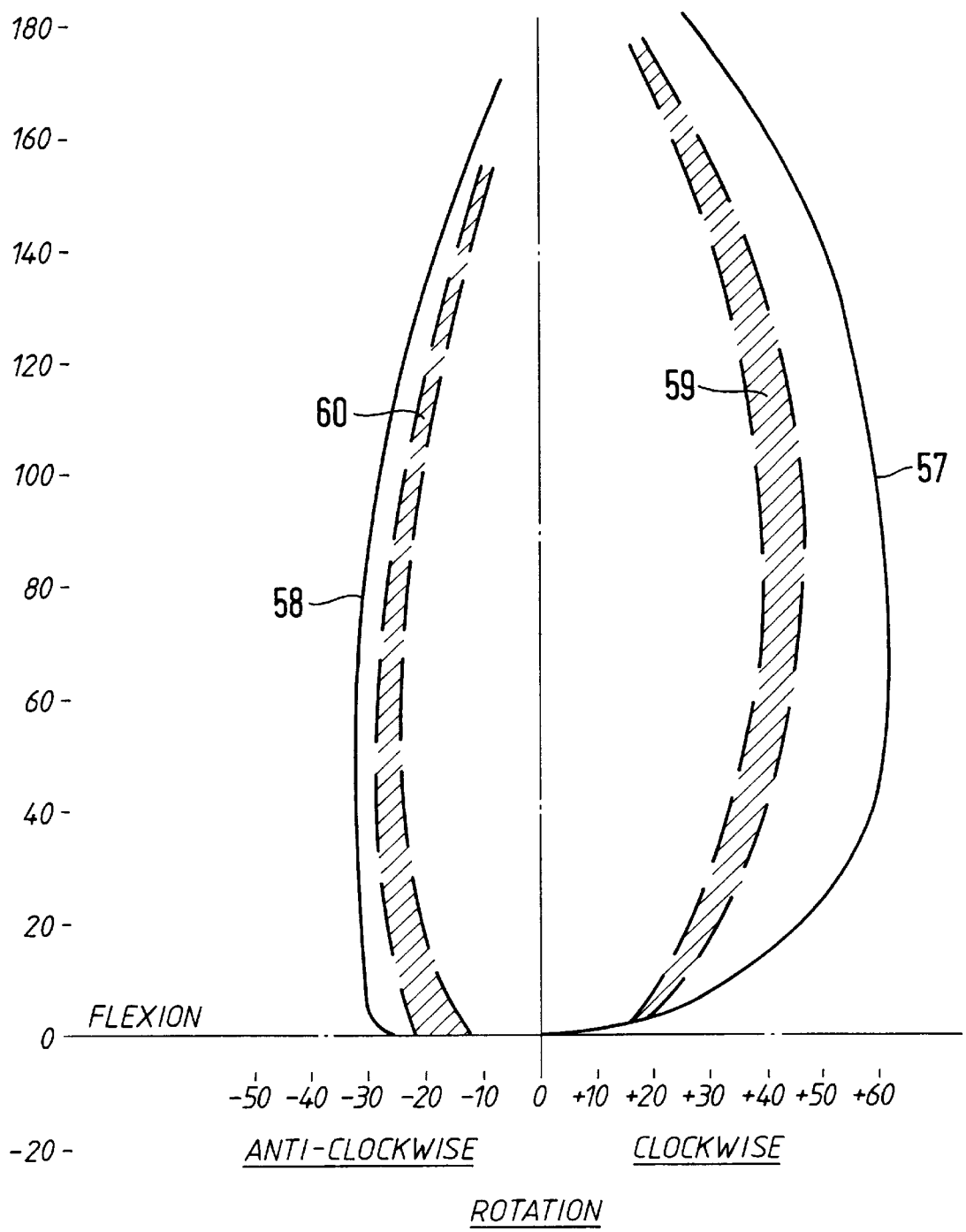
FIG. 12 is a diagram showing rotational angle of the tibia relative to the femur plotted against the angle of flexion of the knee joint both for statistically normal conditions of the knee and for abnormal conditions determined by the user employing the advanced form of the system.

FIG. 12 shows maximum rotation clockwise and anti-clockwise relative to an anterior-posterior plane of the longitudinal axis of the tibia plotted against the angle of flexion, with the actual curves 57 and 58 for an abnormal condition of the knee being shown in full lines and the range of statistical norms being indicated by the hatched bands 59 and 60 between chain lines, as the items might appear upon a video display unit (VDU) employed in place of the LCD module 53. The full-line curves may be produced by the user's first rotating the lower leg to the maximum extent in one sense and then moving the knee through its full range of flexion and then rotating the lower leg to the maximum extent in the opposite sense and moving the knee back through its full range of flexion.

Angular "rotational" movements may be recorded at 5° intervals of flexion of the knee. Since both clockwise and anti-clockwise rotations from a norm or midline are indicated, these are identified as either plus or minus.

If a liquid crystal display (LCD) is used, it could show three sets of angles, for example as:

| Flexion Angle | Internal Rotation | External Rotation |
|---|---|---|
| 15° | 2° | 3° |

In order to obtain both sets of positive or negative angles, two excursions of the flexion angle are performed.

The system can be set to display in various "modes", viz:

Mode 1—Normal

The display will show flexion and rotational angles both positive and negative, and the system acts as a simple angular measuring device.

Any rotation of the patient's tibia will change the readings.

Mode 2—Display and Store

The information/data is stored within an internal memory. Again, two passes are performed to obtain the necessary information.

Mode 3—Review

This facility allows a clinician to review the stored data by stepping through the flexion angle increments and reading off the plus or minus rotation angles.

Two push-button switches are provided marked 'Up' and 'Down' to facilitate stepping through the stored data.

An auto-repeat function is built-in for easy access to specifically required data.

Mode 4—Down Load

This facility is used to transfer the data from the internal memory to a host computer when connected via the interface 50. Once this function has been initiated it cannot be interrupted until complete.

After transmission of the data to the host computer one or more of the following capabilities may be provided:

1: Patient identification and any other relevant information.
2: Recorded data related to the patient.
3: Graphical display of the data.
4: Possible storage of statistical data for comparison, which might be read on the screen simultaneously and from which automatic diagnostic indications might be suggested.
5: Print-out facilities.

A further form of the system includes two identical devices, each as shown in FIGS. 1 to 3, one applied to the tibia externally and the other applied to the femur externally, The one continuously provides a vertical reference for rotation of the tibia, whilst the other continuously provides a vertical reference for rotation of the femur. Electrical signal outputs from the two devices are fed to a computer wherein they are processed and stored. An output from the computer representative of the maximum reasonable angle of rotation by the user of the tibia relative to the femur is displayed, for example upon a liquid crystal display (LCD) and/or a visual display unit (VDU) and/or upon a print-out. It is particularly valuable for the user to measure this maximum angle in the Lachman position (i.e. at about 30° of flexion) or a draw position. To assist the user, there may be simultaneously displayed for comparison the range of normal maximum reasonable angles of rotation of the tibia.

We claim:

1. An apparatus for measuring an angle of turning of one bone of a joint about a substantially horizontal axis, comprising:
    (a) means for determining, said means for determining determining;
        (i) a first angular position of said one bone about said axis, and
        (ii) a second angular position of said one bone about said axis;
    (b) means for mountings, said means for mounting said means for determining upon said one bone; and
    (c) means for automatic displaying, said means for automatic displaying displaying the angle between said first and second angular positions,
    wherein said first and second angular positions are determined relative to the vertical.

2. The apparatus of claim 1, wherein said means for determining comprises one or more devices without mechanically moving parts therein.

3. The apparatus of claim 1, wherein said means for determining measures rotation of said one bone relative to another bone of said joint.

4. The apparatus of claim 1, wherein said means for determining measures flexion/extension of said one bone relative to another bone of said joint.

5. The apparatus of claim 1, wherein:
    (a) said means for determining comprises;
        (i) a first determining device mountable upon said one bone, said first determining device determining said first and second angular positions of said one bone, and
        (ii) a second determining device mountable upon another bone of said joint, said second determining device determining first and second angular positions of said another bone simultaneously with the determining of said first and second angular positions of said one bone by said first determining device, and
    (b) said means for mounting comprises:
        (i) a first mounting device for mounting said first determining device upon said one bone, and
        (ii) a second mounting device for mounting said second determining device upon said another bone,
        there being no mechanical interconnection between said first and second mounting devices through said apparatus.

6. The apparatus of claim 1, wherein said one bone comprises a tibia and said means for mounting carries a single-bar link pivotally mounted at one end upon said means for mounting and carries at its other end a patellar element.

7. The apparatus of claim 1, and further comprising:
(a) means for applying glide force;
(b) a member fixed to said means for mounting;
(c) first and second load cells disposed at respective opposite sides of said member; and wherein:
   (a) said means for applying glide force supports the first and second load cells, and
   (b) said load cells are operable by being pressed against said member by pushing and pulling, respectively, of said means for applying glide force.

8. A method of measuring an angle of turning of one bone of a joint about a substantially horizontal axis, the method comprising:
(a) determining a first angular position of said one bone about said axis,
(b) turning said one bone about said axis,
(c) determining a second angular position of said one bone about said axis, and
(d) automatically displaying the angle between the two positions,
wherein the determining of the first and second angular positions is performed with reference to the vertical.

9. An apparatus for applying and measuring glide force on a tibia of a knee joint, comprising:
(a) means for applying force,
(b) means for mounting carrying said means for applying force so that said means for applying force is movable relative thereto, and
(c) means for analog transducing, the means for analog transducing detecting load applied between said means for applying force and said means for mounting and emitting an electrical signal proportional to the load applied.

10. The apparatus of claim 9, wherein:
(a) said means for applying force comprises a plunger,
(b) said means for mounting has a member fixed thereto and extending transversely of said plunger, and
(c) said means for transducing acts mechanically between said plunger and said member.

11. The apparatus of claim 9 wherein the means for analog transducing comprises a pair of transducers, one of the pair measuring anterior glide force and the other of the pair measuring posterior glide force.

12. An apparatus for measuring an angle of turning of one bone of a joint about a substantially horizontal axis, comprising:
(a) means for determining, said means for determining determining:
   (i) a first angular position of said one bone about said axis, and
   (ii) a second angular position of said one bone about said axis,
(b) means for mounting, said means for mounting mounting said means for determining upon said one bone;
(c) means for automatic displaying, said means for automatic displaying displaying the angle between said first and second angular positions;
wherein:
   (i) said first and second angular positions are determined relative to the vertical;
   (ii) said means for determining comprises:
      (a) a first determining device mountable upon said one bone and determining said first and second angular positions of said one bone, and
      (b) a second determining device mountable upon another bone of said joint and determining first and second angular positions of said another bone simultaneously with the determining of said first and second angular positions of said one bone by said first determining device; and
   (iii) said means for mounting comprises:
      (a) a first mounting device for mounting said first determining device upon said one bone; and
      (b) a second mounting device for mounting said second determining device upon said another bone,
   there being no mechanical interconnection between said first and second mounting devices through said apparatus.

13. An apparatus for measuring an angle of turning of one bone of a joint about a substantially horizontal axis, comprising:
(a) means for determining, said means for determining:
   (i) a first angular position of said one bone about said axis, and
   (ii) a second angular position of said one bone about said axis,
(b) means for mounting, said means for mounting mounting said means for determining upon said one bone;
(c) means for automatic displaying, said means for automatic displaying displaying the angle between said first and second angular positions;
wherein:
   (i) said first and second angular positions are determined relative to the vertical; and
   (ii) said one bone comprises a tibia and said mounting means carries a single-bar link pivotally mounted at one end upon said means for mounting and carries at its other end a patellar element.

14. An apparatus for measuring an angle of turning of one bone of a joint about a substantially horizontal axis, comprising:
(a) means for determining, said means for determining determining:
   (i) a first angular position of said one bone about said axis, and
   (ii) a second angular position of said one bone about said axis,
(b) means for mounting, said means for mounting mounting said means for determining upon said one bone;
(c) means for automatic displaying, said means for automatic displaying displaying the angle between said first and second angular positions;
(d) means for applying glide force;
(e) a member fixed to said means for mounting; and
(f) first and second load cells disposed at respective opposite sides of said member;
wherein:
   (i) said first and second angular positions are determined relative to the vertical;
   (ii) said means for applying glide force supports said first and second load cells, and
   (iii) said load cells are operable by being pressed against said member by pushing and pulling, respectively, of said means for applying glide force.

* * * * *